US010940186B2

(12) United States Patent
Lachmann

(10) Patent No.: US 10,940,186 B2
(45) Date of Patent: *Mar. 9, 2021

(54) TREATMENT OF DISEASES RELATED TO HYPERACTIVITY OF THE COMPLEMENT SYSTEM

(71) Applicant: CAMBRIDGE ENTERPRISE LIMITED, Cambridge (GB)

(72) Inventor: Peter Lachmann, Cambridge (GB)

(73) Assignee: CAMBRIDGE ENTERPRISE LIMITED, Cambridge (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/720,933

(22) Filed: Sep. 29, 2017

(65) Prior Publication Data
US 2018/0021416 A1 Jan. 25, 2018

Related U.S. Application Data

(63) Continuation of application No. 14/753,193, filed on Jun. 29, 2015, now Pat. No. 9,782,460, which is a continuation of application No. 13/256,311, filed as application No. PCT/GB2010/000465 on Mar. 12, 2010, now Pat. No. 9,066,941.

(30) Foreign Application Priority Data

Mar. 13, 2009 (GB) .................................... 0904427

(51) Int. Cl.
| A61K 38/48 | (2006.01) |
| A61P 13/00 | (2006.01) |
| A61P 27/00 | (2006.01) |
| A61P 25/28 | (2006.01) |
| A61P 9/10 | (2006.01) |
| A61K 38/17 | (2006.01) |
| A61K 38/16 | (2006.01) |
| C12N 9/48 | (2006.01) |
| A61K 38/00 | (2006.01) |

(52) U.S. Cl.
CPC .............. *A61K 38/482* (2013.01); *A61P 9/10* (2018.01); *A61P 13/00* (2018.01); *A61P 25/28* (2018.01); *A61P 27/00* (2018.01); *A61K 38/00* (2013.01); *A61K 38/16* (2013.01); *A61K 38/17* (2013.01); *A61K 38/48* (2013.01); *C12N 9/48* (2013.01)

(58) Field of Classification Search
None
See application file for complete search history.

(56) References Cited

U.S. PATENT DOCUMENTS

| 4,883,784 A | 11/1989 | Kaneko et al. |
| 5,132,287 A | 7/1992 | Jensenius |
| 5,221,616 A * | 6/1993 | Kolb .................... G01N 33/564 |
| | | 435/18 |
| 5,378,811 A | 1/1995 | Alsoe et al. |
| 8,569,225 B2 * | 10/2013 | Gilkeson ................ C07K 14/47 |
| | | 435/320.1 |
| 9,066,941 B2 | 6/2015 | Lachmann |
| 2007/0020647 A1 | 1/2007 | Hageman et al. |
| 2007/0238654 A1 | 10/2007 | Deschatelets et al. |
| 2008/0233113 A1 | 9/2008 | Bansal |
| 2008/0269120 A1 * | 10/2008 | McKerracher ......... A61K 47/60 |
| | | 514/1.1 |
| 2008/0318841 A1 | 12/2008 | Chtourou et al. |
| 2009/0015087 A1 | 1/2009 | Rossegger et al. |
| 2009/0118163 A1 | 5/2009 | Gronski et al. |

FOREIGN PATENT DOCUMENTS

| WO | 9105047 A1 | 4/1991 |
| WO | 2009015087 A2 | 1/2009 |
| WO | 2009102085 A1 | 8/2009 |
| WO | 2010103291 A2 | 9/2010 |

OTHER PUBLICATIONS

India Examination Report for copending Indian application 7611/DELN/2011, dated Sep. 27, 2017, 9 pages.
Lachmann et al., "The Demonstration in Human Serum of 'Conglutinogen-Activating Factor' and its Effect on the Third Component of Complement," The Journal of Immunology, 100(4):691-698 (1968).
Lachmann et al., "Further Studies on the C3b Inactivator or Conglutinogen Activating Factor (KAF)," Immunochemistry, 1973, 10:695-700.
Lachmann et al., "The Influence of C3b Inactivator (KAF) Concentration on the Ability of Serum to Support Complement Activation," Clin. Exp. Immunol. (1975) 21:109-114.
Sorensen et al., "Association between the C3F Gene and Atherosclerotic Vascular Diseases," Human Heredity 25:279-283 (1975).
Ziegler et al., "Restoration by Purified C3b Inactivator of Complement-Mediated Function In Vivo in a Patient with C3b Inactivator Deficiency," The Journal of Clinical Investigation, 55:668-672 (1975).
Lachmann, "An Evolutionary View of the Complement System," Behringinst. Mitt., 63:25-37 (1979).
Lachmann et al., "Three rat monoclonal antibodies to human C3," Immunology, 1980, 41:503-515.
Gianazza et al., "A general method for fractionation of plasma proteins," Biochem J. (1982) 201:129-136.
Glover, "Synthetic Peptide Inhibitors of Complement Serine Proteases-1. Identification of Functionally Equivalent Protease Inhibitor Sequences in Serpins and Inhibition of C1s and D," Molecular Immunology 25(12):1261-1267 (1988).

(Continued)

Primary Examiner — Susan M Hanley
(74) Attorney, Agent, or Firm — Patent Law Works, LLP

(57) ABSTRACT

Raising the level of Factor I above physiological levels can be used to treat diseases in which the underlying pathology is linked to overactivity of the C3b-feedback cycle and the generation and pro-inflammatory effects of iC3b. Methods, agents, and compositions for treatment of such diseases are described.

5 Claims, 3 Drawing Sheets

(56) References Cited

OTHER PUBLICATIONS

Duvall-Young et al., "Fundus changes in (type II) mesangiocapillary glomerulonephritis simulating drusen: a histopathological report," British Journal of Ophthalmology, 1989, 73:297-302.
Ostergaard et al., "Pasteurisation of a Factor I (C3b Inactivator) Concentrate from Human Plasma," Vox Sang 1989, 57:240-242.
Sim et al. Methods in Enzymology (1993) 223: 13-35.
Williamson et al., "Virally Inactivated Fresh Frozen Plasma," Vox Sang 1995, 69:159-165.
Wong et al., "Processing of Human Factor I in COS-1 Cells Co-Transfected with Factor I and Paired Basic Amino Acid Cleaving Enzyme (PACE) eDNA," Molecular Immunology, 32(5):379-387 (1995).
Jing et al., "Structures of Native and Complexed Complement Factor D: Implications of the Atypical His57 Conformation and Self-inhibitory Loop in the Regulation of Specific Serine Protease Activity," J. Mol. Biol. (1998) 282:1061-1081.
Ullman et al., "Human complement factor I: its expression by insect cells and its biochemical and structural characterisation," Molecular Immunology 35(1998) 503-512.
Witowski et al. Biochemistry (1999) 38: 11643-11650.
Xia et al, "The -Glucan-Binding Lectin Site of Mouse CR3 (CD11b/CD18) and Its Function in Generating a Primed State of the Receptor That Mediates Cytotoxic Activation in Response to iC3b-Opsonized Target Cells," The Journal of Immunology, 1999; 162:2281-2290.
Burnouf et al., "Nanofiltration of plasma-derived biopharmaceutical products," Haemophilia (2003) 9:24-37.
Dentchev et al., "Amyloid-β found in drusen from some age-related macular degeneration retinas, but not in drusen from normal retinas," Molecular Vision 2003, 9:184-190.
Whisstock et al. Quarterly Rev. Biophysics (2003) 36(3): 307-340.
Morikis et al., "Improvement of the anti-C3 activity of compstatin using rational and combinatorial approaches" Biochemical Society Transactions, Portland Press Ltd. 32:28-32 (2004).
Chica et al. Current Opinion Biotechnology (2005) 16: 378-384.
Yoshida et al., "The potential role of amyloid in the pathogenesis of age-related macular degeneration," The Journal of Clinical Investigation, 115(10):2793-2800 (2005).
Janssen et al., "Structure of C3b reveals conformational changes that underlie complement activity," Nature, 444:213-216 (2006).
Berger et al., "Complement in glomerular injury," Semin Immunopathol (2007) 29:375-384.
De Jorge et al., "Gain-of-function mutations in complement factor Bare associated with atypical hemolytic uremic syndrome," PNAS, 104(1):240-245 (2007).
Pickering et al., "Spontaneous hemolytic uremic syndrome triggered by complement factor H lacking surface recognition domains," JEM, 204(6):1249-1256 (2007).
Rana et al., "Differential leucocyte count and the risk of future coronary artery disease in healthy men and women: the EPIC-Norfolk Prospective Population Study," Journal of Internal Medicine, 262:678-689 (2007).

Richards et al., "Inherited Complement Regulatory Protein Deficiency Predisposes to Human Disease in Acute Injury and Chronic Inflammatory States," Advances in Immunology, 96:141-177 (2007).
Saunders et al., "The Interactive Factor H-atypical hemolytic uremic syndrome mutation database and website: update and integration of membrane cofactor protein and Factor I mutations with structural models" Human Mutation 28:222-234 (2007).
Yates et al, "Complement C3 Variant and the Risk of Age-Related Macular Degeneration," N. Engl. J Med 357 (6):553-561 (2007).
Ding et al., "Targeting Age-related Macular Degeneration with Alzheimer's Disease Based Immunotherapies: Anti-Amyloid-Antibody Attenuates Pathologies in an Age-related Macular Degeneration Mouse Model," Vision Res. 2008, 48(3):339-345.
Kavanagh et al., "Characterization of mutations in complement factor I (CFI) associated with hemolytic uremic syndrome," ScienceDirect, Molecular Immunology 45(2008):95-105, Pergamon GB.
Nilssons et al., "Molecular and functional analysis of complement factor I mutations in atypical haemolytic ureamic syndrome patients" Molecular Immunology 45:4131 (2008).
Rodriguez De Cordoba et al., "Translational Mini-Review Series on Complement Factor H: Genetics and disease associations of human complement factor H," Clinical and Experimental Immunology, 151:1-13 (2008).
Rose et al., "Factor I is required for the development of membranoproliferative glomerulonephritis in factor H-deficient mice," The Journal of Clinical Investigation, 118(2):608-618 (2008).
Wang et al. J. Immunol. (2008) 181: 712-720.
Wang et al., "Altered Function of Factor I Caused by Amyloid β: Implication for Pathogenesis of Age-Related Macular Degeneration from Drusen," The Journal of Immunology, 2008:181:712-720.
Zetterberg et al., "Association of Complement Factor H Y402H Gene Polymorphism With Alzheimer's Disease," American Journal of Medical Genetics Part B (Neuropsychiatric Genetics) 147B:720-726 (2008).
Lachmann, "The Amplification Loop of the Complement Pathways," Advances in Immunology, 104:115-149 (2009).
Lambert et al., "Genome-wide association study identifies variants at CLU and CRI associated with Alzheimer's disease," Nature Genetics, 41(10):1094-1100 (2009).
Wang et al., "Amyloid-β Up-Regulates Complement Factor B in Retinal Pigment Epithelial Cells Through Cytokines Released From Recruited Macrophages/Microglia: Another Mechanism of Complement Activation in Age-Related Macular Degeneration," Journal of Cellular Physiology, 220:119-128 (2009).
Nilsson et al. Molecular Immunology (2011) 48: 1611-1620.
PCT International Search Report, PCT/GB2010/000465, dated Nov. 19, 2010.
PCT International Written Opinion, PCT/GB2010/000465, dated Nov. 19, 2010.
PCT International Preliminary Report on Patentability, PCT/GB2010/000465, dated Sep. 13, 2011.

* cited by examiner

Effect of increased FI concentration on C3 conversion by inulin and by aggregated IgG. (■) Inulin (7 mg/ml). (▲) Inulin (0·3 mg/ml). (●) Aggregated IgG.

TREATMENT OF DISEASES RELATED TO HYPERACTIVITY OF THE COMPLEMENT SYSTEM

CROSS-REFERENCE TO RELATED APPLICATIONS

This application is a continuation of U.S. patent application Ser. No. 14/753,193, filed Jun. 29, 2015, which will issue as now U.S. Pat. No. 9,782,460 issued Oct. 10, 2017, which is a continuation of U.S. patent application Ser. No. 13/256,311, filed Dec. 5, 2011, now U.S. Pat. No. 9,066,941, issued Jun. 30, 2015, which was a national phase entry under 35 U.S.C. § 371 of International Patent Application PCT/GB2010/000465, filed Mar. 12, 2010, designating the United States of America and published in English as International Patent Publication WO 2010/103291 A2 on Sep. 16, 2010, which claims the benefit under Article 8 of the Patent Cooperation Treaty to Great Britain Patent Application Serial No. 0904427.2, filed Mar. 13, 2009, the disclosure of each of which is hereby incorporated herein in its entirety by this reference.

TECHNICAL FIELD

This application relates to agents, compositions and methods for the prevention, treatment, or amelioration of diseases in which the underlying pathology is linked to overactivity of the C3b-feedback cycle and the generation and pro-inflammatory effects of iC3b, a product of the activation of the complement system.

BACKGROUND

The complement system comprises a set of about 30 proteins that may be located in the fluid phase (generally, in plasma) or on the surfaces of cells in which the proteins are expressed. The system serves several important biological functions related to both innate and adaptive immunity and is phylogenetically ancient. It must recognize foreign (non-self) entities, react to them in a highly amplifiable way in order to trigger an effective defensive biological response and yet keep the system under tight control to avoid collateral ("self") damage. The components may be grouped into eight functional classes:

1. Recognition molecules that bind to pathogen-associated molecular patterns not found in the host organism (e.g., bacterial carbohydrate) or to antigens defined through previous encounter or as part of the pre-existing immunoglobulin repertoire. An example is Mannan-binding lectin (MBL).
2. Central non-enzymatic effector proteins that undergo combinations and transformations critical to the system (e.g., C3, C4).
3. Central enzymatic effectors that also participate in these processes (e.g., C1 esterase, C2, Factor B).
4. Amplifiers of the activation processes either enzymatic (Factor D) or non-enzymatic (Properdin).
5. Terminal components that do not undergo feedback processes but give rise to the final cytolytic membrane attack complex (components C5 to C9).
6. Soluble negative regulators either enzymatic (Factor I) or non-enzymatic (e.g., Factor H, C4bp).
7. Negative regulators located on the surfaces of cells that they protect against attack by the endogenous complement system (e.g., CR1, DAF, MCP, CD59).
8. Receptors that permit cellular signaling by products of complement activation, thus linking the process to other immune and cell regulatory functions (e.g., CR2, CR3, C3a, C5a receptor).

Although the general functions of the complement system have been known for several decades, the details of the processes, their evolution and regulation and the relationship of the system to cellular immunity are more recent scientific achievements. These developments can be summarized as follows (from P. J. Lachmann (1979), An evolutionary view of the complement system, Behring Inst. Mitt. no. 63 25-37):

1. The archaeo-complement system probably consisted of a form of the C3 protein alone—this was cleaved by microbial proteases into C3a and C3b. The small C3a fragment is a chemotactic factor. The large fragment, C3b, acquires briefly the capacity to attach covalently to the microbe following cleavage of its thiol ester group. Bound C3b acts as an "opsonization marker" marking the microbe for destruction by phagocytic cells. The recent determination of the crystal structures of C3 and C3b (B. J. C. Janssen et al., *Nature* 444: 213-6, 2006) has shown how the thiol ester is buried within the multi-domain C3 molecule and is exposed in C3b following a major rearrangement of the domains.
2. The complement system achieved a primary level of amplification through addition of the protease Factor B, which mediates positive feedback by combining with the C3b product to form a complex, C3bB that, after cleavage by microbial or other proteases, forms a convertase, C3bBb, capable of activating more C3.
3. This system was further amplified to create the current "alternative pathway" or "C3b feedback" loop by recruiting Factor D, a protease probably used for other purposes and that is only active when its substrate, Factor B, is complexed to C3b. FD resists all plasma protease inhibitors and allows the C3b feedback cycle to function in plasma.
4. Together with Properdin, these components created the basis of the rapid and highly amplified response to external pathogens. Addition of the lectin and "classical" (antibody-triggered) systems followed.
5. The corresponding control system to prevent excessive C3b generation in higher vertebrates with pumped blood circulation was provided by a soluble plasma protease (FI), which catalyzes the cleavage of C3b to iC3b (the "First clip"). Factor I will cleave C3b only when this is complexed to a molecule with "Factor I cofactor activity." In plasma the principal molecule with this property is Factor H.
6. iC3b cannot participate in convertase formation and, hence, amplification, but it can function as a powerful pro-inflammatory agent through interaction with complement receptor type 3 (CR3, CD11b/CD18), an integral membrane protein found on neutrophils and monocytes that engages iC3b, a reaction enhanced by also binding microbial carbohydrate (e.g., beta glucan, (Y. Xia, V. Vetvicka, J. Yan, M. Hanikýrová, T. Mayadas, and G. D. Ross (1999), the beta-glucan-binding lectin site of mouse CR3 (CD11b/CD18) and its function in generating a primed state of the receptor that mediates cytotoxic activation in response to iC3b-opsonized target cells, *J. Immunol.* 162 (4):2281-90).
7. iC3b can be further broken down by Factor I (FI) and the membrane-bound cofactor CR1 (CD35) in a so-called "Second clip," which yields C3d,g-a C3 fragment, which is not pro-inflammatory (it does, however, have an effect on the adaptive immune system through stimulation of specific antibody production through interaction with CR2) and C3c.

These processes are illustrated in FIG. 1. This shows an outline of the activation of the complement system initiated by recognition events at the beginning of the pathways and amplified by the C3b amplification loop—the generation and deactivation of iC3b. The C3b amplification loop is also shown in FIG. 2. This amplification loop is a balance between two competing cycles both acting on C3b: the C3 feedback cycle that enhances amplification, and the C3 breakdown cycle that down-regulates it. It is solely the balance between their rates of reaction on which amplification depends. The C3 breakdown cycle generates iC3b as its primary reaction product. iC3b, through its reaction with the leukocyte integrins (and complement receptors) CR3 (CD11b/CD18) and CR4 (CD11c/CD18), is the most important mechanism by which complement mediates inflammation.

BRIEF SUMMARY

The disclosure is derived from the understanding that the genetic predisposing factors for several inflammatory diseases all serve to enhance the activity of the C3b feedback cycle, thereby creating a pro-inflammatory phenotype of which the formation of iC3b and its reaction with CR3 is a critical component.

According to the disclosure, there is provided a method of preventing, treating, or ameliorating a disease associated with overactivity of the complement C3b feedback cycle, which comprises increasing the level of C3b-inactivating and iC3b-degradation activity in a subject to a level that exceeds a normal level of C3b-inactivating and iC3b-degradation activity.

According to the disclosure, there is also provided an agent (or agents) with C3b-inactivating and iC3b-degradation activity for use as a medicament.

According to the disclosure, there is further provided an agent (or agents) with C3b-inactivating and iC3b-degradation activity for use in the prevention, treatment, or amelioration of a disease associated with overactivity of the complement C3b feedback cycle, at a dosage that increases the level of C3b-inactivating and iC3b-degradation activity in a subject to a level that exceeds a normal level of C3b-inactivating and iC3b-degradation activity.

According to the disclosure, there is further provided use of an agent (or agents) with C3b-inactivating and iC3b-degradation activity in the manufacture of a medicament for the prevention, treatment, or amelioration of a disease associated with overactivity of the complement C3b feedback cycle, at a dosage that increases the level of C3b-inactivating and iC3b-degradation activity in a subject to a level that exceeds a normal level of C3b-inactivating and iC3b-degradation activity.

The term "complement C3b feedback cycle" is used herein to refer to a positive feedback cycle acting through C3b (the major product of C3 cleavage), which interacts with factors B and D of the alternative pathway to form a C3-cleaving enzyme.

"Overactivity of the complement C3b feedback cycle," means that there is increased formation of the C3-cleaving enzyme compared with a normal subject, with consequent increased turnover of C3 and components of the alternative pathway. The turn-over of C3 can be measured in-vivo using $^{125}$I-labelled C3. Alternatively turn-over of C3 can be measured indirectly in-vitro by determining the rate of C3 conversion to iC3b when a small complement activating stimulus is given (as described in P. J. Lachmann and L. Halbwachs (1975), the influence of C3b inactivator (KAF) concentration on the ability of serum to support complement activation, *Clin. Exp. Immunol.* 21:109).

Preferably, the disease is associated with an ongoing predisposition to overactivity of the C3b feedback cycle. This means that whenever the complement system is activated during the course of the disease, there is an overactivity of the C3b feedback cycle. This is distinguished over diseases in which there may be a temporary susceptibility to overactivity of the C3b feedback cycle, for example, during a particular phase of the disease. Factor I and Factor H have been reported to be decreased in the pre or early phases of the exacerbation stage, but not during most of the regression stage of systemic lupus erythematosus (SLE).

Preferably, the disease is an inflammatory disease.

Preferably, the disease is not an autoimmune disease, especially SLE, rheumatoid arthritis or glomerulonephritis.

Examples of diseases that may be prevented, treated, or ameliorated by methods of the disclosure are Age-related Macular Degeneration (AMD), atypical hemolytic uremic syndrome (aHUS), membranoproliferative glomerulonephritis Type 2 (MPGN2), atherosclerosis (in particular, accelerated atherosclerosis), chronic cardiovascular disease, and Alzheimer's disease (particularly Alzheimer's disease in a subject carrying an ApoE4 allele, i.e., a subject who is heterozygous or homozygous for the ApoE4 allele).

The subject may have a genetic predisposition to the disease with or without a family history of the disease. Accordingly, methods of the disclosure may further comprise determining whether the subject has a genetic predisposition to the disease or a family history of the disease, and administering appropriate prophylaxis or therapy depending on the result of the determination.

Examples of genetic predispositions to diseases associated with overactivity of the complement C3b feedback cycle (preferably, an ongoing predisposition to overactivity of the C3b feedback cycle) are: a mutation in Factor H that reduces its ability to function as a Factor I cofactor compared with wild-type Factor H; a mutation in Factor H that reduces its binding to C3b compared with wild-type Factor H; homozygous Factor H deficiency; a mutation in membrane cofactor protein (MCP) that reduces its function compared with wild-type MCP; heterozygous Factor I deficiency; a gain-of-function mutation in Factor B; or a C3F allotype.

All the predisposing alleles share the property of enhancing the activity of the C3b amplification loop by either upregulating the C3b feedback cycle or downregulating the C3b breakdown cycle. They all, therefore, promote a hyperinflammatory complement phenotype. This will produce its effects by increasing the production of C5a and of the membrane attack complex and, most importantly, by the increased production of iC3b, which, through its reaction with CR3 (CD11b/CD18) and CR4 (CD11c/CD18) on neutrophils, monocytes and NK cells, provides complement's most powerful pro-inflammatory mechanism.

The term "agent with C3b-inactivating and iC3b-degradation activity" is used herein to mean an agent with serine protease activity that is able to catalyze the cleavage of C3b to iC3b (the "First Clip") and degradation of iC3b (the "Second Clip"). The agent may require one or more cofactors in order to catalyze these reactions. For example, Factor H may be required for the First Clip, and CR1 may be required for the Second Clip.

A preferred example of the agent is Factor I. However, other agents with functional equivalence to Factor I may alternatively be used, such as fragments or derivatives of Factor I that retain C3b-inactivating and iC3b-degradation activity. The Factor I, or fragment or derivative, may be plasma-derived Factor I, or recombinant Factor I, or fragment or derivative. Preferably, the Factor I is of the same species as the subject.

The skilled person will appreciate that derivatives of Factor I that retain C3b-inactivating and iC3b-degradation activity may be prepared by providing a protein comprising a sequence that differs from native Factor I sequence by one or more conservative amino acid substitutions, and/or by deletion of one or more amino acid residues. Preferably, such Factor I derivatives retain at least 60% amino acid identity across the entire length of the sequence with native Factor I. More preferably, a Factor I derivative retains at least 70%, 80%, 90%, or 95% amino acid identity across the entire length of the sequence with native Factor I.

It is also envisaged that the agent could be provided in a form that requires modification (for example, prior to administration, or in vivo) to provide the C3b-inactivating and iC3b-degradation activity. It is also envisaged that the C3b-inactivating and iC3b-degradation activity could each be provided by separate agents, which may be administered together or separately (for example, sequentially).

One or more agents with C3b-inactivating and iC3b-degradation activity may be administered. Preferably, the agent(s) is(are) not administered with Factor H.

Preferably, the subject has a normal level of C3b-inactivating and iC3b-degradation activity provided by the subject's Factor I. A normal level is regarded to be in the range 30-40 µg/ml Factor I in the subject's plasma.

Measurement of plasma Factor I can be determined using conventional methods, for example, antigenically, using radial immunodiffusion, "rocket" electrophoresis, or nephelometry or functionally, using conglutinin (Lachmann and Muller-Eberhard, 1968, *J. Immunol.* 100:691), or a hemolytic inhibition assay (Lachmann, Nicol and Aston, 1973, *Immunochem.* 10:695).

Preferably, the level of C3b-inactivating and iC3b-degradation activity in the subject's plasma is increased by at least 10% above the normal level, preferably for a period of at least one to two weeks. However, the level of activity in the subject's plasma is preferably increased by no more than 50%, preferably no more than 25% above the normal level.

Preferably, the level of activity is increased by administering an agent(s) with C3b-inactivating and iC3b-degradation activity to the subject. The agent is preferably used at a dosage for increasing the level of activity in the subject's plasma by at least 10% above the normal level, preferably for a period of at least one to two weeks. However, the dosage preferably increases the level of activity in the subject's plasma by no more than 50%, preferably no more than 25% above the normal level.

The agent (preferably Factor I) is preferably used at a dosage up to 20 mg/kg, for example, 0.001 or 0.05 mg/kg to 20 mg/kg, more preferably less than 6 mg/kg, for example, 0.001 or 0.05 mg/kg to less than 6 mg/kg, more preferably up to 1.5 mg/kg, for example, 0.001, 0.05, or 0.2 mg/kg to 1.5 mg/kg or 0.001, 0.05, or 0.2 mg/kg to 1 mg/kg, or less than 1 mg/kg, for example, 0.001, 0.05, or 0.2 mg/kg to less than 1 mg/kg. Preferred doses for human subjects are up to 250 mg, for example, 6.5 or 10 mg to 250 mg, preferably less than 50 mg, for example, from 6.5 or 10 mg to less than 50 mg, or 10-20 mg. For systemic administration, the agent may preferably be administered at a dosage up to 250 mg, for example, from 6.5 or 10 mg to 250 mg, preferably from 6.5 or 10 mg to less than 50 mg, for example, 10-20 mg. For intravenous or intramuscular administration, the agent may preferably be administered at a dosage of 0.05 to 20 mg/kg, for example, 0.05 to less than 6 mg/kg, or 0.05 to less than 1 mg/kg. For intraocular administration the agent may be administered a dosage of 0.001 to 1 mg/eye Factor I.

The level of activity may be increased by administering C3b-inactivating and iC3b-degradation activity at least once per month, or at least once per day.

It will be appreciated that the appropriate frequency of administration of C3b-inactivating and iC3b-degradation activity will depend on many factors, including the route of administration, the type of disease and the severity, stage of the disease, the plasma half life of the C3b-inactivating and iC3b-degradation activity in the preparation (the plasma half life of Factor I is believed to be approximately one week), the background factor I levels in the patient, the desired steady-state protein concentration level, the influence of any therapeutic agents used in combination with the treatment method of the disclosure, the age, health, and sex of the subject. In many cases, it will be appropriate to monitor progress of the disease to determine the effect of the treatment, and based on the results determine whether or not treatment should be continued, and the appropriate frequency of the treatment.

If the disease is an acute disease, such as atypical hemolytic uremic syndrome (aHUS), C3b-inactivating and iC3b-degradation activity is preferably administered if the subject is determined to be suffering from an infection or a fever. Progress of the aHUS may be monitored by the blood platelet count, the presence of red cell fragments in the blood, the presence of raised levels of lactate dehydrogenase (LDH) in the blood, or the concentration of urea or creatinine in the blood, and/or by the enumeration in urine of red blood cells, white blood cells, and casts and measurement of urinary protein.

If the disease is a chronic disease, such as Age-related Macular Degeneration (AMD), C3b-inactivating and iC3b-degradation activity is preferably administered every 2 to 4 weeks. Progress of AMD may be monitored by determining the extent of drusen formation (deposits that accumulate beneath the retinal pigmented epithelium). If the extent of drusen formation is reduced, or if the rate of drusen formation is reduced by the treatment, then the frequency of administration of the C3b-inactivating and iC3b-degradation activity may also be reduced.

Alternatively, or additionally the progress of AMD may be monitored by measuring in vivo the amount of C3 fragments bound in the retina. This may be achieved, for example, by administering a binding agent that binds to iC3b but not to C3 or C3b. Preferably, the binding agent is a monoclonal antibody or a fragment or derivative thereof that retains binding specificity for iC3b. It will be appreciated that the monoclonal antibody or fragment or derivative should not induce an adverse immune reaction in the subject to whom it is administered. Thus, it may be desirable to use a humanized monoclonal antibody, or a derivative such as a single chain Fv, where the subject is a human subject.

Preparation of a monoclonal antibody that binds iC3b (but not native C3 or C3b) is described in Lachmann et al. (*Immunology*, 1980, 41 (3):503-515—Clone 9). This antibody is available commercially from Hycult Biotechnology b.v. (Catalog no. HM2199, Monoclonal antibody to human C3g, clone 9, also known as YB2/90-5-20; the antibody recognizes iC3b, C3dg and C3g in plasma, but does not recognize C3 or C3b). A single chain Fv derived from YB2/90-5-20 may be used as a suitable binding agent for administration to a human subject.

The binding agent should be labeled so that it can be detected. In a preferred embodiment, the binding agent is labeled with fluorescein. After intravenous injection, this will stain deposits in the eye, which can then be quantitated by fluorography.

It will be appreciated that binding agents that bind to iC3b, but not to C3 or C3b, may be used for the diagnosis of an inflammatory lesion in the eye, for example, as a result of Age-related Macular Degeneration (AMD).

According to the disclosure, there is provided a method for diagnosing whether a subject has an inflammatory lesion in an eye, which comprises administering a binding agent that binds to iC3b, but not to C3 or C3b, to the subject, and determining whether the binding agent binds to the retina in the eye of the subject.

Presence of binding agent bound at the retina in the eye of the subject indicates that the subject has an inflammatory lesion in that eye.

According to the disclosure, there is further provided a method for monitoring progression of an inflammatory lesion in an eye of a subject, which comprises administering to the subject a binding agent that binds to iC3b, but not to C3 or C3b, at a first point in time and at a subsequent second point in time, and determining the amount of binding agent that binds to the retina in an eye of the subject at the second point in time relative to the first point in time.

An increase in the amount of binding agent that binds to the retina at the second point in time relative to the first point in time indicates that the inflammatory lesion has progressed in the subject. No change in the amount of binding agent that binds to the retina at the second point in time relative to the first point in time indicates that the inflammatory lesion has not progressed in the subject. A decrease in the amount of binding agent that binds to the retina at the second point in time relative to the first point in time indicates that the inflammatory lesion has regressed in the subject.

It will be appreciated that methods of the disclosure for monitoring progression of an inflammatory lesion may be used to determine the effectiveness of treatment of the inflammatory lesion in the subject.

There is also provided, according to the disclosure, use of a binding agent that binds to iC3b, but not to C3 or C3b, to diagnose an inflammatory lesion in an eye of a subject, or to monitor the progression of an inflammatory lesion in an eye of a subject.

The disclosure further provides a kit for diagnosing whether a subject has an inflammatory lesion, or for monitoring the progression of an inflammatory lesion, in an eye of the subject, which comprises a binding agent that binds to iC3b, but not to C3 or C3b, and instructions for diagnosing whether the subject has an inflammatory lesion, or for monitoring the progression of an inflammatory lesion, in an eye of the subject using the binding agent. The instructions may describe administration of the binding agent to the subject and/or how to determine whether the binding agent binds to the retina in an eye of the subject.

The binding agent may be labeled with a label that allows detection of the binding agent at the retina. A suitable label is a fluorescent label, for example, a fluorophore such as fluorescein.

The binding agent may be administered systemically, preferably intravenously, to the subject.

There is also provided, according to the disclosure, a composition comprising a binding agent that binds to iC3b, but not to C3 or C3b, together with a pharmaceutically acceptable carrier, excipient, or diluents. The composition is preferably suitable for systemic, preferably intravenous administration.

The binding agent is preferably a monoclonal antibody or a fragment or derivative of a monoclonal antibody.

According to the disclosure, there is also provided a fragment or derivative of a monoclonal antibody that binds to iC3b, but not to C3 or C3b. Preferably, the derivative is a single chain Fv (scFv), for example, an scFv of YB2/90-5-20. Preferably, the fragment or derivative is labeled, suitably with a fluorescent label, for example, a fluorophore such as fluorescein.

Such fragments or derivatives may be used as binding agents in methods or kits of the disclosure for the diagnosis of an inflammatory lesion, or for monitoring the progression of an inflammatory lesion, in an eye of a subject.

Methods and kits of the disclosure for the diagnosis of an inflammatory lesion, or for monitoring the progression of an inflammatory lesion, in an eye of a subject may be used for the diagnosis of AMD, or for monitoring the progression of AMD, in the subject.

In preferred aspects of the disclosure, the subject is a human subject. However, it may alternatively be desired to ameliorate, treat, or prevent (or diagnose or monitor progression of) the disease in non-human animals, such as domestic pets.

There is further provided, according to the disclosure, a unit dose comprising an agent or agents with C3b-inactivating and iC3b-degradation activity for administration to a subject.

There is also provided, according to the disclosure, a pharmaceutical composition in unit dose form, which comprises an agent or agents with C3b-inactivating and iC3b-degradation activity, and a pharmaceutically acceptable carrier, excipient, or diluent for administration to a subject.

There is also provided, according to the disclosure, a pharmaceutical composition, which comprises an agent or agents with C3b-inactivating and iC3b-degradation activity, and a pharmaceutically acceptable carrier, excipient, or diluent for administration to a subject.

There is further provided, according to the disclosure, a unit dose for, or adapted for intraocular administration, which comprises an agent or agents with C3b-inactivating and iC3b-degradation activity.

There is further provided, according to the disclosure, a pharmaceutical composition, preferably in unit dose form, for or adapted for intraocular administration, which comprises an agent or agents with C3b-inactivating and iC3b-degradation activity, and a pharmaceutically acceptable carrier, excipient, or diluent.

There is further provided, according to the disclosure, a unit dose for, or adapted for systemic administration, which comprises an agent or agents with C3b-inactivating and iC3b-degradation activity. The unit dose for, or adapted for, systemic administration should be sterile, and free of pyrogens and viruses.

There is further provided, according to the disclosure, a pharmaceutical composition, preferably in unit dose form, for or adapted for systemic administration, which comprises an agent or agents with C3b-inactivating and iC3b-degradation activity, and a pharmaceutically acceptable carrier, excipient, or diluent.

Systemic administration is preferably intravenous or intramuscular administration.

A unit dose or composition of the disclosure may comprise up to 250 mg, for example, from 1 or 10 mg to 250 mg, preferably less than 50 mg, for example, from 1 or 10 mg to less than 50 mg, preferably 10-20 mg, of an agent or agents with C3b-inactivating and iC3b-degradation activity.

There is further provided, according to the disclosure, a unit dose or composition of the disclosure for, or adapted for, administration to a human subject.

A unit dose or composition of the disclosure may be in solid form, preferably lyophilized form.

Preferably, the agent of the unit dose or composition of the disclosure is Factor I, or a fragment or derivative of Factor I that retains C3b-inactivating and iC3b-degradation activity. The Factor I, or fragment or derivative, may be plasma-derived Factor I, or recombinant Factor I, or fragment or derivative.

BRIEF DESCRIPTION OF THE DRAWINGS

Preferred embodiments of the disclosure are described below with reference to the accompanying drawings in which.

DETAILED DESCRIPTION

Figure 1:
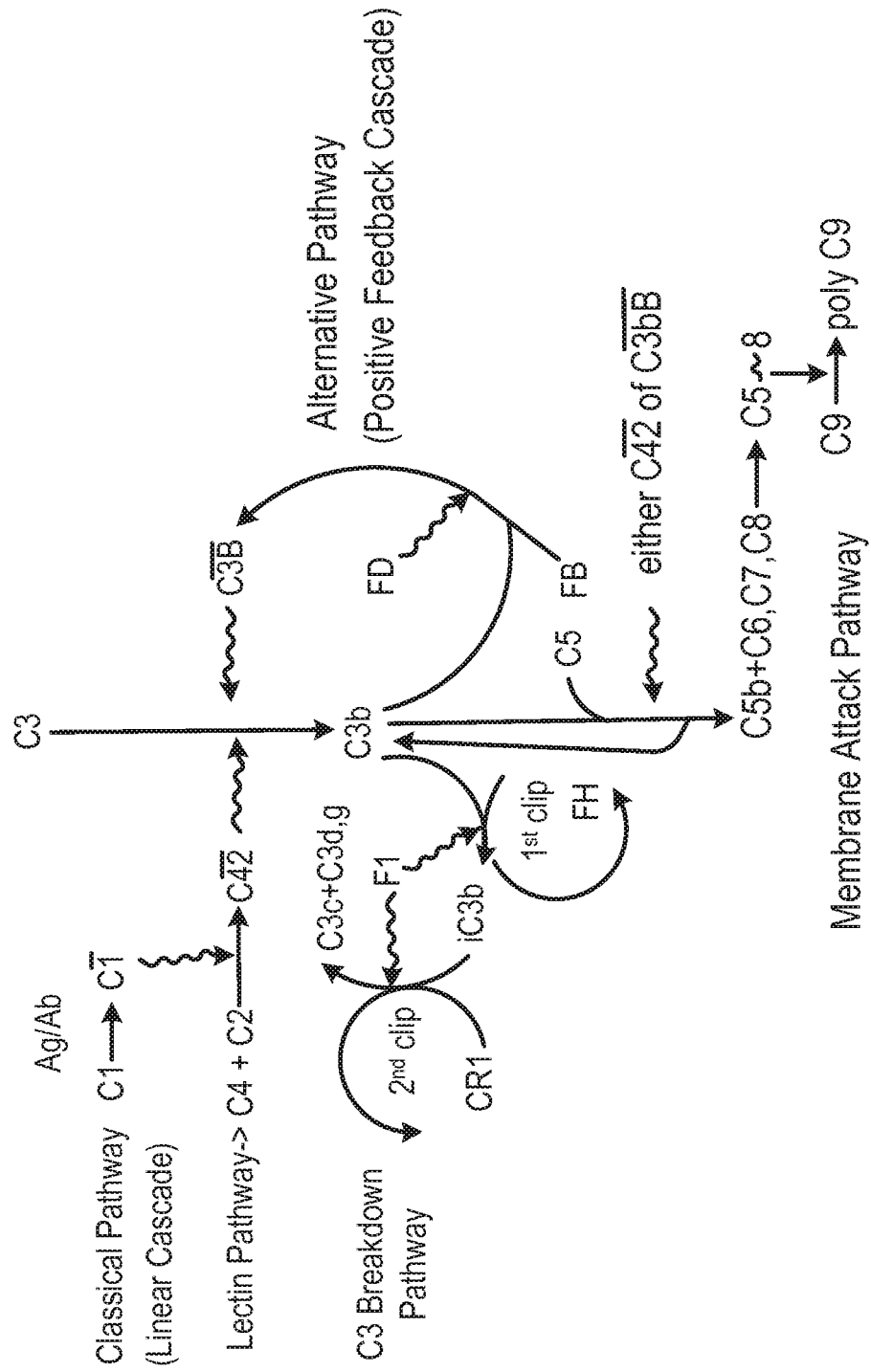
FIG. 1 shows an outline of the activation of the complement system initiated by recognition events at the beginning of the pathways and amplified by the C3b amplification loop—the generation and deactivation of iC3b and the dependence of those events on Factor I, Factor I cofactors and Factor H is noted.
Figure 2:
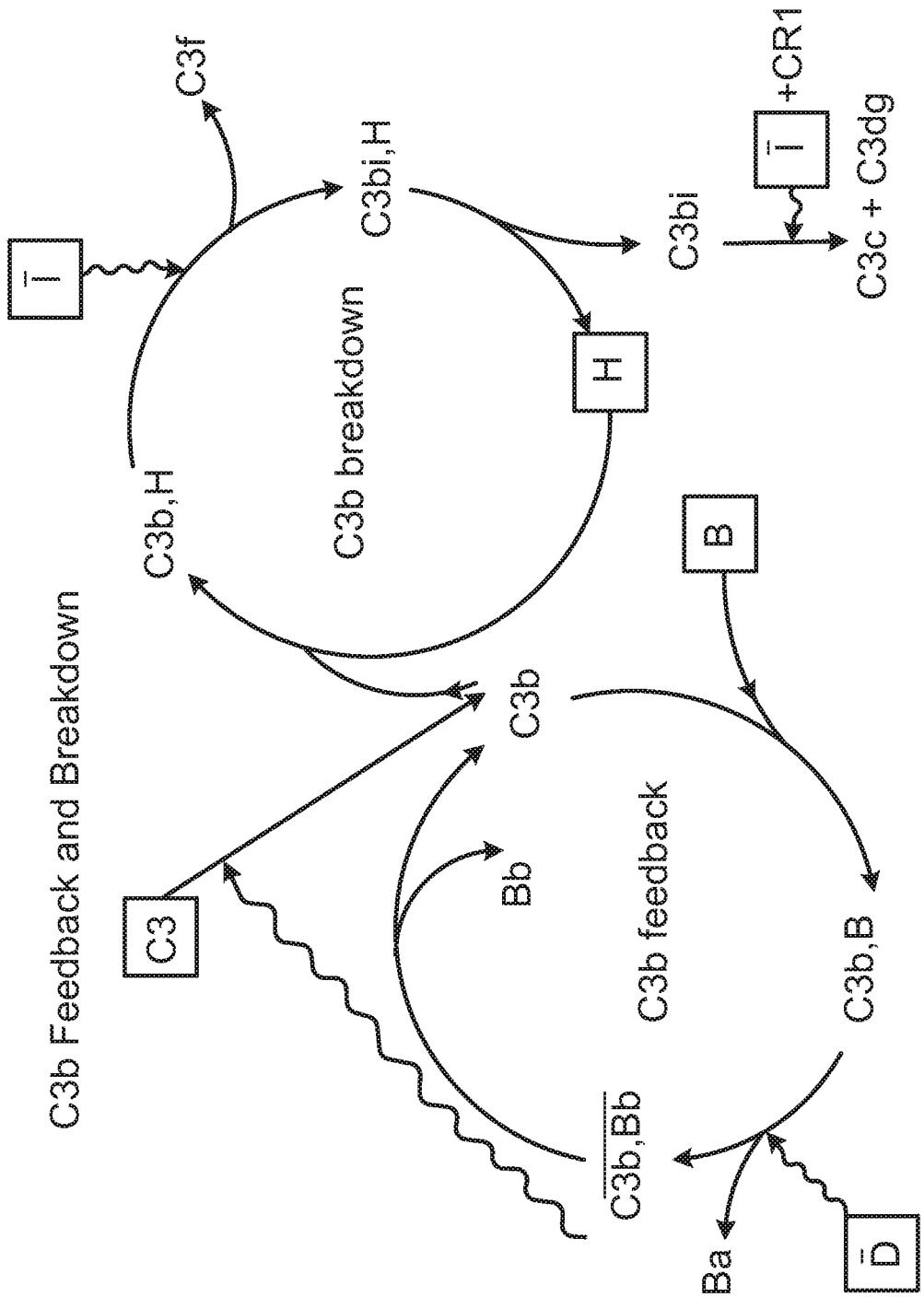
FIG. 2 shows the C3b amplification loop, which is a balance between two separate and competing pathways—the C3b feedback cycle and the C3b breakdown cycle.

In a preferred embodiment, the disclosure provides for a therapy that by raising Factor I concentration reduces the activity of the C3b-feedback cycle.

1. Disease-Associations of Aberrant Complement Activation

Recent gene-association studies have shown a strong influence of complement system components in several diseases and conditions, with most attention having focused on Age-related Macular Degeneration (AMD) and atypical hemolytic uremic syndrome (aHUS), the latter having, so far, been more extensively studied.

Thus:

Mutations in Factor H that give reduced function as a Factor I co-factor or reduce its binding to C3b predispose to AMD and aHUS. Homozygous Factor H deficiency also has been associated with aHUS as have autoantibodies to Factor H.

Mutations in the cell-bound complement control protein, membrane cofactor protein (MCP or CD46) that give reduced function predispose to aHUS.

(The extensive literature on these associations is reviewed in A. Richards, D. Kavanagh, and J. P. Atkinson (2007), Inherited Complement Regulatory Protein Deficiency Predisposes to Human Disease in Acute Injury and Chronic Inflammatory States, The Examples of Vascular Damage in Atypical Hemolytic Uremic Syndrome and Debris Accumulation in Age-Related Macular Degeneration, *Adv. Immunol.* 96:141-77.)

Heterozygous deficiency of Factor I (but not homozygous (total) Factor I deficiency) is associated with aHUS (D. Kavanagh, A. Richards, M. Noris, R. Hauhart, M. K. Liszewski, D. Karpman, J. A. Goodship, V. Fremeaux-Bacchi, G. Remuzzi, T. H. Goodship, and J. P. Atkinson (2008), characterization of mutations in complement factor I (CFI) associated with hemolytic uremic syndrome, *Mol. Immunol.* 95-105).

Gain-of-function mutations in complement factor B are associated with atypical haemolytic uraemic syndrome (E. Goicoechea de Jorge, C. L. Harris, J. Esparza-Gordillo, L. Carreras, E. A. Arranz, C. A. Garrido, M. Lopez-Trascasa, P. Sanchez-Corral, B. P. Morgan, and S. Rodriguez de Cordoba (2007), mutations in Factor B that increase its function as a C3-convertase predispose to aHUS, *Proc. Natl. Acad. Sci. U.S.A.* 104 (1):240-5).

The C3F allotype is associated with an increased risk of AMD (J. R. Yates, T. Sepp, B. K. Matharu, J. C. Khan, D. A. Thurlby, H. Shahid, D. G. Clayton, C. Hayward, J. Morgan, A. F. Wright, A. M. Armbrecht, B. Dhillon, I. J. Deary, E. Redmond, A. C. Bird, and A. T. Moore (2007), complement C3 variant and the risk of age-related macular degeneration, *N. Engl. J. Med.* 357:553-61). There is also a long-standing finding that C3F carries an increased risk of atherosclerotic vascular disease (H. Sorensen and J. Dissing (1975), association between the C3F gene and atherosclerotic vascular diseases, *Hum. Hered.* 25 (4):279-83).

C3F augments the C3b-feedback cycle by forming a more active C3-convertase (C. Harris and B. P. Morgan personal communication).

In mice, membranoproliferative glomerulonephritis Type 2 (MPGN2, a renal inflammatory condition), occurs spontaneously in Factor H knockout (k/o) mice and results in consumption of C3, and iC3b deposition in glomeruli. If such k/o mice are then made to express a mutant form of FH functionally equivalent to the FH mutant associated with aHUS in man, they develop aHUS but not MPGN2 (M. C. Pickering, E. G. de Jorge, R. Martinez-Barricarte, S. Recalde, A. Garcia-Layana, K. L. Rose, J. Moss, M. J. Walport, H. T. Cook, S. R. de Cordoba, and M. Botto (2007), spontaneous hemolytic uremic syndrome triggered by complement factor H lacking surface recognition domains, *J. Exp. Med.* 204 (6):1249-56). Thus both aHUS and MPGN2 are due to subtle differences in Factor H control of C3b breakdown.

FI knockout mice do not show C3b deposition on their glomeruli despite having all their plasma C3 converted to C3b because of unrestrained action of the C3b-feedback cycle. Mice with both FI and Factor H deficiency also do not develop MPGN2. However, injection of FI into the double k/o animals restores the MPGN2 pattern of C3 deposition in the glomeruli. This experiment demonstrates conclusively that conversion of C3b to iC3b is absolutely required for the development of the inflammatory renal disease (K. L. Rose, D. Paixao-Cavalcante, J. Fish, A. P. Manderson, T. H. Malik, A. E. Bygrave, T. Lin, S. H. Sacks, M. J. Walport, H. T. Cook, M. Botto, and M. C. Pickering (2008), Factor I is required for the development of membranoproliferative glomerulonephritis in factor H-deficient mice, *J. Clin. Invest.* 2008 February; 118 (2):608-18; January 17 [Epub ahead of print].

These disturbances of C3b feedback thus predispose to some relatively acute renal conditions (such as aHUS and MPGN2) that occur in early life as well as more chronic conditions (e.g., AMD) that occur later in life. It, therefore, appears to be the case that the existence of a genetically determined systemic pro-inflammatory complement phenotype allows progressive damage to occur in end-organs as a cumulative result of multiple episodes of complement activation. This type of damage can occur much earlier in life in the kidneys than it does in the eye.

AMD, Complement and Alzheimer's Disease: the possibility that there might be some association between AMD and Alzheimer's disease was raised by Dentchev et al. (T. Dentchev, A. H. Milam, V. M. Lee, J. Q. Trojanowski, and J. L. Dunaief (2003), amyloid-beta is found in drusen from some age-related macular degeneration retinas, but not in drusen from normal retinas, *Mol. Vis.* 9:184-190) who reported that β amyloid protein could be found in the drusen from some AMD retinas but was not found in drusen from normal retinas. They suggested that β amyloid, the protein associated with the characteristic deposits in Alzheimer's disease might also play a role in AMD. This suggestion gained support from the work of Yoshida et al. (T. Yoshida, K. Ohno-Matsui, S. Ichinose, T. Sato, N. Iwata, T. C. Saido, T. Hisatomi, M. Mochizuki, and I. Morita (2005), the potential role of amyloid beta in the pathogenesis of age-related macular degeneration, *J. Clin. Invest.* 115 (10):2793-2800) who studied the effects of β amyloid protein on retinal pigment endothelial cells in vitro and showed the accumulation of this protein gave rise to some of the features characteristic of AMD, including retinal pigment epithelium atrophy and basal deposit formation, as well as affecting the balance between VegF and PDF.

It was, therefore, of considerable interest when it was reported by Zetterberg et al. (M. Zetterberg, S. Landgren, M. E. Andersson, M. S. Palmer, D. R. Gustafson, I. Skoog, L. Minthon, D. S. Thelle, A. Wallin, N. Bogdanovic, N. Andreasen, K. Blennow, and H. Zetterberg (2008), association of complement Factor H Y402H gene polymorphism with Alzheimer's disease, *Amer. J. Med. Genet. Part B (Neuropsychiatric Genet.)* 147B:720-726) that there was an association of the Factor H Y402H allele (which carries an increased risk of AMD) also with Alzheimer's disease. However, the association with Alzheimer's disease was evident only in those individuals also carrying the ApoE4 allele, which is known to be a strong predisposing genetic influence for Alzheimer's disease. This was the first indication that a genetic predisposition to AMD was also associated with Alzheimer's disease.

A possible mechanism by which β amyloid might alter complement function in the eye was reported by Wang et al. (J. Wang, K. Ohno-Matsui, T. Yoshida, A. Kojima, N. Shimada, K. Nakahama, O. Safranova, N. Iwata, T. C. Saido, M. Mochizuki, and I. Morita (2008), altered function of Factor I caused by amyloid β: implication for pathogenesis of age-related macular degeneration from drusen, *J. Immunol.* 181:712-720) who found that β amyloid was able to inhibit Factor I function. This intriguing observation would benefit from some further studies to determine the stoichiometry of the reaction and whether the inhibition is competitive. Such inhibition of Factor I would provide a mechanism by which the deposition of β amyloid protein at a local site would give rise to a hyperinflammatory effect by reducing the activity of the C3 breakdown pathway. Even more recently, it has been reported by Wang et al. (J. Wang, K. Ohno-Matsui, T. Yoshida, N. Shimada, S. Ichinose, T. Sato, M. Mochizuki, and I. Morita (2009), amyloid-β up-regulates complement Factor B in retinal pigment epithelial cells through cytokines released from recruited macrophages/microglia: another mechanism of complement activation in age-related macular degeneration, *J. Cel. Physiol.* 220:119-128) that β amyloid also upregulates the production of Factor B in retinal pigment epithelium cells. It apparently does this by recruiting microglia, which then produce cytokines that increase the production of Factor B. This would again produce a local hyperinflammatory state by increasing the activity of the C3b feedback cycle.

These reports support the idea that β amyloid protein may play a role in the pathogenesis of AMD by affecting the activities on the C3 feedback and breakdown cycles, in both cases promoting the hyperinflammatory phenotype. Also supporting such a connection is the finding that antibodies to β amyloid protein attenuate disease in a mouse model of AMD (J. D. Ding, J. Lin, B. E. Mace, R. Herrmann, P. Sullivan, and C. B. Rickman (2008), targeted age-related macular degeneration with Alzheimer's disease based immunotherapies: anti-amyloid-β antibody attenuates pathologies in an age-related macular degeneration mouse model, *Vis. Res.* 48:339-345). Further support for the role of the amplification loop in Alzheimer's disease is the very recent report of Lambert et al. (2009) (genome-wide association study identifies variants at CLU and CR1 associated with Alzheimer's disease, *Nat. Genet.* September 6 (Epub ahead of print)) of whole genome associations in Alzheimer's disease, which showed a modest association (odds ratio 1.21 95%, confidence interval 1.14-1.29) with CR1.

These findings on the effects of β amyloid protein on the complement amplification loop raise the possibility that these same mechanisms may also be at work in Alzheimer's disease and that here too it could be advantageous to down-regulate the hyperinflammatory complement phenotype, particularly in those who carry the ApoE4 allele.

2. Therapeutic Considerations

The above analysis suggests that diseases such as aHUS and AMD might be tackled by targeted intervention in the C3b feedback and iC3b generation pathways.

Raising the concentration of FI by infusion of purified enzyme is the preferred strategy for so doing. It is known that quite modest augmentation of Factor I concentration in human plasma strikingly inhibits C3b feedback whether this is initiated by an alternative pathway activator (particulate inulin) or by a classical pathway activator (aggregated IgG) (P. J. Lachmann and L. Halbwachs (1975), the influence of C3b inactivator (KAF) concentration on the ability of serum to support complement activation, *Clin. Exp. Immunol.* 21:109). Furthermore, raising Factor I concentration will also accelerate iC3b breakdown to C3dg and C3c and thereby reduce the inflammatory effects due to its reaction with CR3.

The alternative strategy of raising plasma Factor H concentrations by infusion of this protein will also dampen feedback activity by providing more cofactor activity for the conversion of C3b to iC3b (the "first clip") but will lead to an increased level of iC3b since it has no co-factor activity for the FI mediated breakdown of iC3b (the "second clip"). Only the complement receptor CR1 (CD35) has this co-factor activity in-vivo.

Inhibiting the amplifier enzyme Factor D provides a mechanism to reduce the formation of C3b but has no effect on the formation or breakdown of iC3b. Genetic deficiency of Factor D in man does not give rise to kidney disease In terms of practical therapy, the Factor I strategy is also more attractive because the plasma concentrations of FI are relatively low (equivalent to about 35 mg/litre in man) whereas addition of exogenous Factor H would require at least 10 times as much protein. Pharmacological inhibition of Factor D has been attempted (e.g., G. I. Glover et al., *Mol. Immunol.* 1988, 25:1261-7) and compounds based on 3,4 dichloroisocoumarin or isatoic anhydride were found to be effective inhibitors of the enzyme but with insufficient selectivity to be viable drugs (e.g., H. Jing et al., *J. Mol. Biol.* 1998, 282:1061-81).

This disclosure is, therefore, based on the therapeutic use of recombinant or plasma-derived FI. Early studies on addition of exogenous FI in experimental systems suggested that supplementation probably needed to increase blood levels by no more than 25% (Lachmann and Halbwachs (1975)). Based on the gene association studies noted above, it is likely that a chronic increase in FI plasma concentration of perhaps as little as 10% could have therapeutic effects if other mechanistic conditions were met. This would imply doses in man in the region of 10-20 mg of protein administered systemically at intervals of several weeks (see J. B. Ziegler, C. A. Alper, F. S. Rosen, P. J. Lachmann and L. Sherington (1975), restoration by purified C3b inactivator of complement-mediated function in vivo in a patient with C3b inactivator deficiency, *J. Clin. Invest.* 55:668).

In the case of aHUS, a plausible protocol would be to give a dose of Factor I to a genetically predisposed patient whenever he/she has an infection or a fever of any cause. The same treatment would similarly be given to any patient who has already had one attack of aHUS independent of their genotype.

In the case of AMD, it would probably be advisable to give the FI regularly every 2-4 weeks as soon as drusen have been detected or even earlier where there is a genetic predisposition and a family history.

Subjects with evidence of atherosclerotic vascular disease that is more severe than would be expected from the Framingham predictions could also benefit from damping down their complement system particularly if they have any of the genetic predispositions described above. In this connection the findings of the EPIC-Norfolk study that, in healthy middle-aged subjects, a raised neutrophil count (a surrogate marker for a pro-inflammatory phenotype) is a predictor of earlier mortality (J. S. Rana, S. M. Boekholdt, P. M. Ridker, J. W. Jukema, R. Luben, S. A. Bingham, N. E. Day, N. J. Wareham, J. J. Kastelein, and K. T. J. Khaw (2007), differential leucocyte count and the risk of future coronary artery disease in healthy men and women: the *EPIC-Norfolk Prospective Population Study Intern Med.* 262 (6):678-89) are also significant. There should be benefit in treating subjects in the top decile of neutrophils counts prophylactically with FI as soon as they show any signs of atherosclerotic vascular disease.

3. Specific Embodiments of the Disclosure

The large-scale isolation of the FI from Cohn Fractions 3 and 4 of human plasma has been accomplished using affinity chromatography on columns coupled with an anti-FI monoclonal antibody and may also be carried out using other specific chromatography methods that have been applied to plasma products such as those employing dye ligands (see, for example, E. Gianazza and P. Arnaud (1982), a general method for fractionation of plasma proteins, dye-ligand affinity chromatography on immobilized Cibacron blue F3-GA, *Biochem J.* 201:129-36). Factor I can be sterilized by ultrafiltration/nanofiltration (T. Burnouf and M. Radosovich (2003), nanofiltration of plasma-derived biopharmaceutical products, *Haemophilia* 24-37) and/or viral destruction in plasma feedstock (L. M. Williamson and J. P. Allain (1995), virally inactivated fresh frozen plasma, *Vox Sang.* 69:159-65) or heating of the purified product or concentrate (also K. L. and J. Kihl (1989), pasteurization of a factor I (C3b inactivator) concentrate from human plasma, *Vox Sang.* 57:240-2).

Production of recombinant human FI protein has also been reported from baculovirus/insect cells (C. G. Ullman, D. Chamberlain, A. Ansari, V. C. Emery, P. I. Haris, R. B. Sim, S. J. Perkins (1998), human complement factor I: its expression by insect cells and its biochemical and structural characterization, *Mol. Immunol.* 35:503-12) and from COS and CHO cells. (M. J. Wong, G. Goldberger, D. E. Isenman, J. O. Minta (1995), processing of human factor I in COS-1 cells co-transfected with factor I and paired basic amino acid cleaving enzyme (PACE) cDNA, *Mol. Immunol.* 32:379-87).

The factor I materials of this disclosure may be formulated into pharmaceutical compositions comprising a carrier suitable for the desired delivery method. Suitable carriers include any material that, when combined with this protein, retains the function of the protein and is non-reactive with the subject's immune systems. Examples include any of a number of standard pharmaceutical carriers such as sterile phosphate buffered saline solutions, bacteriostatic water, and the like (see, generally, *Remington: The Science and Practice of Pharmacy*, 2005 (21st Edition, Popovich, N (eds), Advanced Concepts Institute, University of the Sciences in Philadelphia, Pa.).

One or more human factor I formulations may be administered via any route capable of delivering the protein to the disease site. Routes of administration include, but are not limited to, intravenous, intraocular, intraperitoneal, intramuscular, intradermal and the like. Factor I preparations may be lyophilized and stored as a sterile powder, preferably under vacuum, and then reconstituted in bacteriostatic water containing, for example, benzyl alcohol preservative, or in sterile water prior to injection. Treatment will generally involve the repeated administration of the protein preparation via an acceptable route of administration such as intravenous (IV) or intraocular (IO) injection at an effective dose.

Dosages will depend upon various factors generally appreciated by those of skill in the art, including the route of administration, the type of disease and the severity, stage of the disease, the plasma half life of the protein in the preparation (the plasma half life of Factor I is believed to be approximately one week), the background factor I levels in the patient, the desired steady-state protein concentration level, and the influence of any therapeutic agents used in combination with the treatment method of the disclosure.

A typical normal plasma concentration of Factor I in man is about 35 micrograms/ml. Allowing an extracellular fluid volume of about 10 liters gives a total of 350 mg Factor I. To raise this acutely by 10% would take 35 mg; to raise it by 25% would take 88 mg. Preferred amounts of Factor I are up to three times this amount, for example, up to 100-250 mg every 1-3 weeks.

For IV or intramuscular administration, doses are likely to range from about 0.05 to 20 mg/kg with a frequency of dosing between daily and monthly as repeated administrations may be required to achieve disease inhibition or regression. IO administration will involve significantly lower doses in the likely range of 1 to 1000 micrograms/eye. A determining factor in defining the appropriate dose is the amount of a particular preparation necessary to be therapeutically effective in a particular disease context and this can only be determined by clinical investigation.

Patients may be evaluated for plasma factor I levels during therapy in order to assist in the determination of the most effective dosing regimen and related factors. Conventional assay methods based on breakdown of C3b or C4b in the presence of a cofactor may be used for quantifying circulating factor I in patients prior to or during treatment.

EXAMPLE

The Influence of Factor I (FI) Concentration on the Ability of Serum to Support Complement Activation
Materials and Methods Inulin—a standard suspension (50 mg/ml) in saline was sonicated. Dilutions of this suspension were made, the final concentration of inulin in the serum being given for each experiment.

Aggregated human γ-globulins—these were obtained by heating a concentrated solution (27 mg/ml) of human γ-globulins at 63° C. for 15 minutes.

Factor I—functionally purified FI was prepared from the euglobulin fraction of serum by DEAE-cellulose and Sephadex G-200 chromatography (Lachmann, Aston and Nicol, 1973). The titer of the purified FI standard solution was measured and compared to the normal serum titer by its capacity of inducing EAC143 agglutination in presence of bovine conglutinin (Lachmann, and Muller-Eberhard, 1968). Variations in FI concentration in normal human serum were obtained by adding different dilutions of the purified FI standard solution to the serum.

Figure 3:
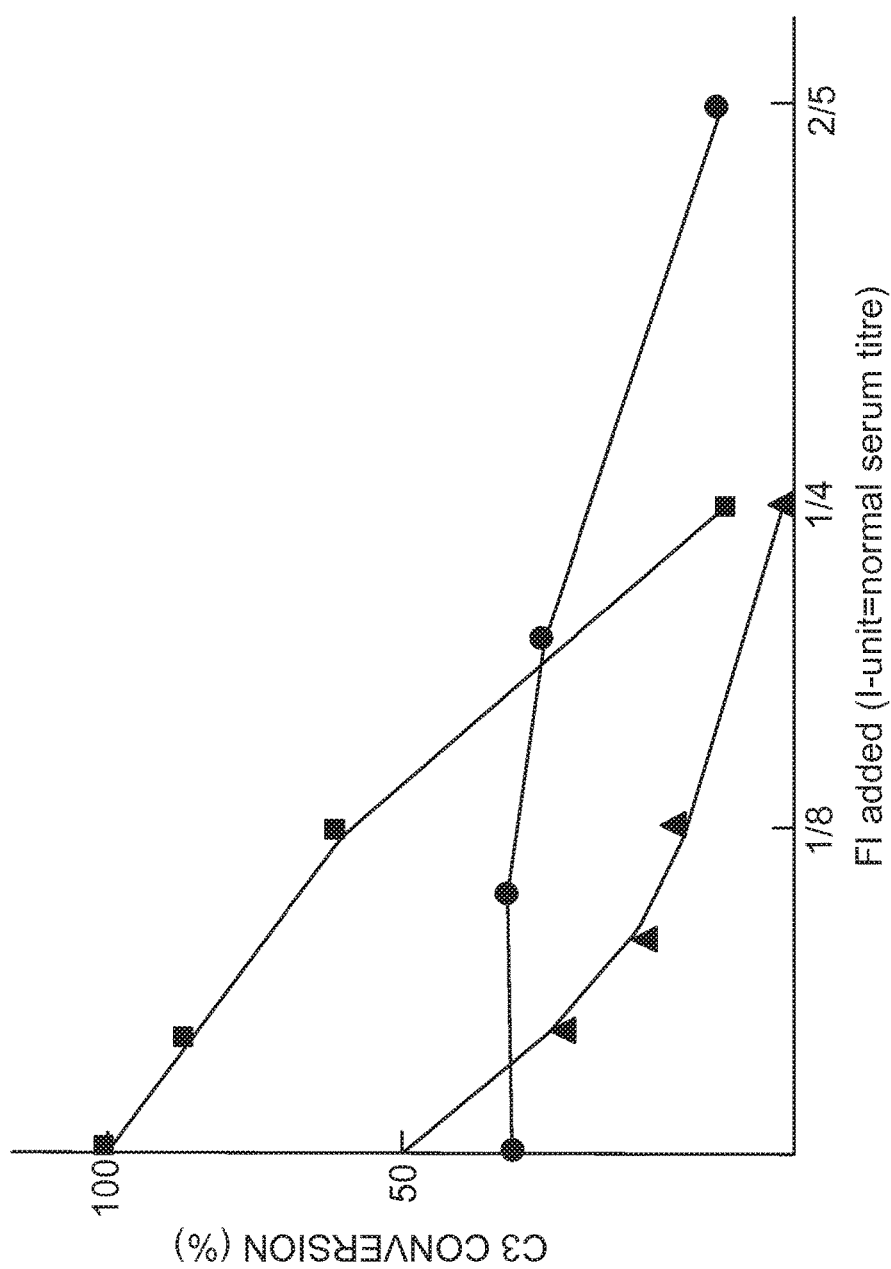
FIG. 3 shows the effect of increased factor I (FI) concentration on C3 conversion by inulin and by aggregated IgG.

Effect of Increased FI Concentration on Complement Activation by Inulin (FIG. 3).

FI inhibits C3 conversion by inulin at all concentrations of inulin used. It also inhibits factor B conversion by inulin. Quite small amounts of FI are sufficient for this inhibitory effect: an increase of only 15% of the normal FI concentration in the serum results in 50% inhibition of C3 conversion by inulin.

Effects of Increased FI Concentration on Complement Activation by Aggregated γ-Globulins (FIG. 3).

C3 conversion by aggregated γ-globulins is also by increased FI concentration, but in this case more than 20% increase is necessary in order to observe the inhibition.

CONCLUSION

It is clear from the experiments described that the FI concentration in whole human serum is by no means so high that further elevation has no effect on complement activities. In fact, quite modest increases in the FI concentration (15-25%) markedly inhibit the capacity of a typical properdin pathway activator like inulin and (to a slightly lesser extent) of a typical classical pathway activator like aggregated human IgG to produce complement activation. This evidence suggests that variations in FI concentration even within physiological limits may significantly modulate complement activation.

REFERENCES

Lachmann, P. J., W. P. Aston, and P. A. E. Nicol (1973), *Immunochemistry* 10:695;
Lachmann, P. J., and H. J. Muller-Eberhard (1968), *J. Immunol.* 100:691.

What is claimed is:

1. A method for treating Age-related Macular Degeneration (AMD) or atypical Hemolytic Uremic Syndrome (aHUS) in a human subject which comprises lowering the amount of C3b activity in a subject, the method comprising:
   administering a pharmaceutical composition comprising a therapeutically effective amount of an agent selected from native Factor I and a polypeptide that has at least 90% amino acid identity with native Factor I and that retains C3b-inactivating activity and iC3b degrading activity, and does not comprise Factor H, to the human subject;
   wherein administration of the pharmaceutical composition increases the level of C3b-inactivating activity and iC3b degrading activity in the human subject to a level that exceeds a normal level of C3b-inactivating activity and iC3b degrading activity in the human subject;
   thereby treating AMD or aHUS in the human subject.

2. The method according to claim 1, wherein the level of C3b-inactivating activity and iC3b degrading activity is increased by at least 10% above the normal level.

3. The method according to claim 1, wherein the level of C3b-inactivating activity and iC3b degrading activity is increased by no more than 50% above the normal level.

4. The method according to claim 1, wherein the subject has a normal level of C3b-inactivating activity and iC3b degrading activity prior to increasing the level of C3b-inactivating activity and iC3b degrading activity in the subject.

5. The method according to claim 1, wherein the level of C3b-inactivating activity and iC3b degrading activity in an eye of the subject is increased to a level that exceeds a normal level of C3b-inactivating activity and iC3b degrading activity in an eye of the subject.

* * * * *